United States Patent [19]
Golberstein

[11] Patent Number: 5,103,106
[45] Date of Patent: Apr. 7, 1992

[54] REFLECTIVE OPTICAL INSTRUMENT FOR MEASURING SURFACE REFLECTANCE

[76] Inventor: Moshe Golberstein, 2100 Drew Ave. So., Minneapolis, Minn. 55416

[21] Appl. No.: 672,317

[22] Filed: Mar. 20, 1991

Related U.S. Application Data

[63] Continuation-in-part of Ser. No. 580,824, Sep. 11, 1990.

[51] Int. Cl.$^5$ .......................................... G01N 21/86
[52] U.S. Cl. ..................................... 250/571; 356/448
[58] Field of Search .................... 250/571, 572, 561; 356/445–448, 375, 376, 378

[56] References Cited

U.S. PATENT DOCUMENTS

| | | | |
|---|---|---|---|
| 3,858,983 | 1/1975 | Foster et al. | 356/448 |
| 4,072,425 | 2/1978 | Guttman | 356/447 |
| 4,358,202 | 11/1982 | Puffer et al. | 250/571 |
| 4,673,818 | 1/1987 | Guerra | 250/571 |
| 4,737,650 | 4/1988 | West | 250/571 |
| 4,929,846 | 5/1990 | Mansour | 250/571 |
| 4,933,567 | 6/1990 | Silva | 250/572 |

Primary Examiner—David C. Nelms
Assistant Examiner—S. Allen
Attorney, Agent, or Firm—James V. Harmon

[57] ABSTRACT

An optical instrument for measuring characteristics of a specimen comprising a light source to project a beam onto the surface of a specimen at a selected oblique angle of incidence $\beta$. The instrument also contains a photosensor to receive the beam reflected from the specimen at the same angle $\beta$. A conductor connected to the photosensor is provided for carrying current to signal conditioning hardware used to compare the current from two or more photosensors or, if present, from different segments of the same photosensor to provide information concerning the specimen. Photosensor means is also positioned facing the specimen on an optical axis located normal to the surface of the specimen and intermediate the incident and reflected beams from the light source to receive a beam reflected from the specimen normal to its surface, i.e., along the optical axis. Signals from the photosensors are fed to the signal conditioning hardware to measure the optical power and to compare signals for measuring characteristics of the surface, e.g., its reflectivity or reflectance and to locate its position and/or orientation with respect to the instrument.

17 Claims, 3 Drawing Sheets

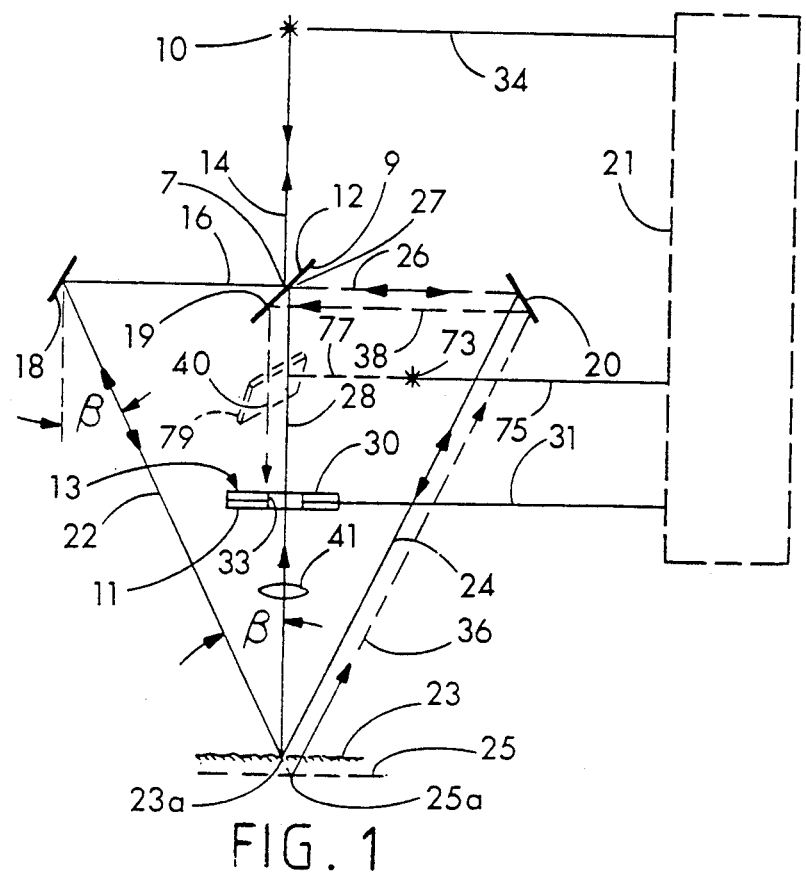
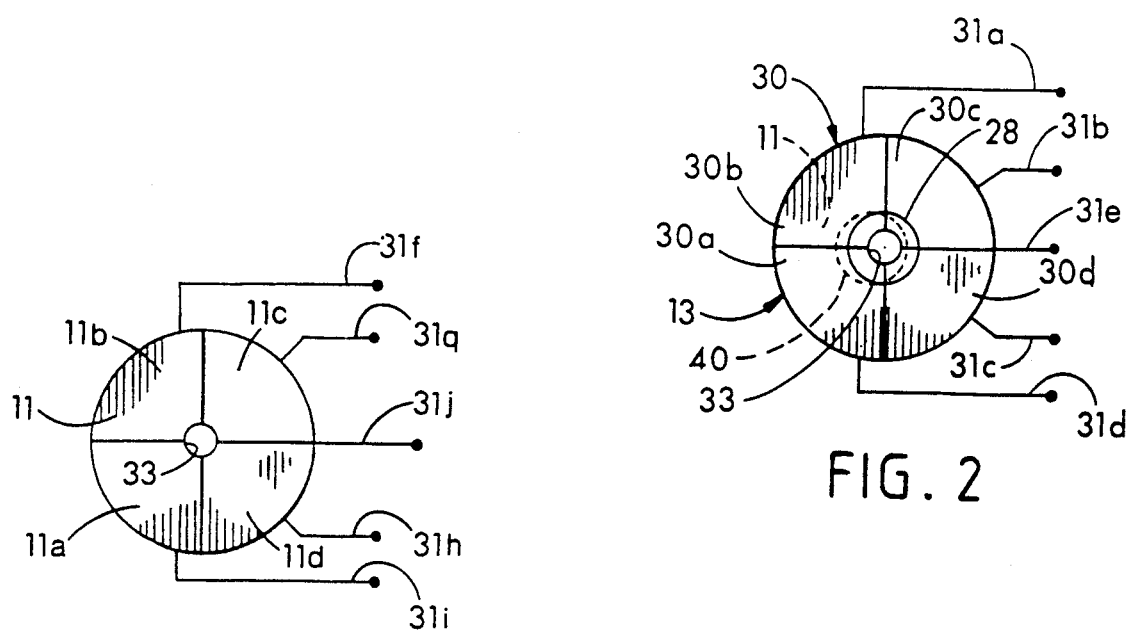

REFLECTIVE OPTICAL INSTRUMENT FOR MEASURING SURFACE REFLECTANCE

This is a continuation-in-part of my prior application Ser. No. 07/580,824 filed Sep. 11, 1990 and bearing the same title.

FIELD OF THE INVENTION

The present invention relates to optical instrumentation and more particularly to optical instruments for conducting measurements and particularly measurements from reflective surfaces.

BACKGROUND OF THE INVENTION

There are many methods currently in use to measure surface reflectance and surface roughness. Some methods were described in the background paragraph of my prior U.S. Pat. No. 4,770,536. Other methods are based upon triangulation and interferometric principles. While the Reflective Photometry Instrument described in U.S. Pat. No. 4,770,536 does measure reflectance, its performance is further enhanced by introduction of additional features to be described below. One major objective of the present invention is to provide a controllable distance, e.g. a constant distance, and if desired, a constant angle between the instrument and the surface under examination at which surface reflectance or emission can be measured.

SUMMARY OF THE INVENTION

Briefly, the invention provides an optical instrument for measuring characteristics of a specimen. The instrument includes a light source to project a beam onto the surface of a specimen at a selected oblique angle of incidence $\beta$. The instrument also contains a photosensor to receive the beam reflected from the specimen at the same angle $\beta$. Conductors connected to the photosensor are provided for carrying signals to signal conditioning hardware used to compare the signals from two or more photosensors or from different segments of the same photosensor to provide information concerning the specimen. Photosensor means is also preferably positioned to face the specimen on an optical axis located normal to the surface of the specimen and intermediate the incident and reflected beams from the light source to receive a beam from the specimen normal to its surface, i.e., along the optical axis. Signals from the photosensors are fed to the signal conditioning hardware to measure the optical power and to compare signals for measuring characteristics of the surface, e.g., its reflectivity or reflectance and to locate its position and/or orientation with respect to the instrument.

GENERAL DESCRIPTION OF THE INVENTION

While not essential, it is preferred that the photosensors are segmented to provide additional information concerning the surface being studied, particularly since it is difficult to be certain in all cases that the light beam is normal to the surface of the photosensor. It is also preferred that the photosensors are apertured to allow portions of the incident beams to pass through the photosensors.

More specifically, one preferred form of the invention provides a non-contact instrument for determining a distance between a reference point typically within the instrument and a test or target surface, i.e. the surface of a workpiece. Such a distance will be referred to herein as a "standoff distance." Once the instrument is positioned in a known standoff distance from the target surface or workpiece, it can then measure the reflectance of the surface, for example as described using prior U.S. Pat. No. 4,770,536. An instrument made according to the present invention can be made to utilize either of two modes of operation. One mode is based upon reflective/refractive optics principles. The other is based upon interferometric principles. The physical embodiment of instruments utilizing these two different principles are similar in architecture and employ most of the same components. The components common to both instruments are: a collimated light source to provide a longitudinal or axial beam defining an optic axis, preferably at least two non-axial mirrors to receive the beam reflected laterally from the axial beam, and a photosensor. In a preferred form of the invention, each photosensor is an apertured, double-sided segmented photosensor. The instrument is connected during use to suitable signal conditioning hardware.

In addition to the above mentioned components, when the instrument is to use reflective/refractive principles it contains an axially located mirror. On the other hand, when the instrument is to employ interferometric principles, an axial beam splitter is used in place of the axial mirror and a pair of apertured segmented photosensors are preferably provided. Both the mirror and beam splitter comprise axial reflective members. The light source for an interferometric instrument is a coherent monochromatic source with known polarization characteristics. The interferometric instrument utilizes a combination of different beam paths to produce interfering beams which are detected by the photosensors.

Performance of both types of instruments can be further improved, if desired, by additional lenses and other components known in the art. By way of example, such optional components include quarter wave plates, polarizers, additional isolators (Faraday type, for example), lenses, drivers for micrometric displacement of mirrors (such as PZT translators for example), and shutters. The instrument of the present invention has an internal dimensional reference point that is established by the longitudinal axial beam and its intersection with the double-sided mirror or the beam splitter, as the case may be. Major components of the instrument are set at predetermined distances from this point.

When the longitudinal axial beam emanating from the light source encounters the first surface, i.e., the upper surface, of the double-sided mirror, it is deflected toward one of the non-axial mirrors. This second mirror is positioned at an inclined angle in such a way that the beam deflected by it to the target surface under evaluation so as to form an angle $\beta$ in relation to the surface under evaluation. The surface under evaluation deflects the beam toward a third mirror (the second non-axial mirror) which is positioned laterally of the double-sided mirror. The third mirror is positioned in such a way that it establishes a selected angle between the beam reflected from the target surface under evaluation and the beam deflected from the third mirror. The beam deflected from the third mirror (the second non-axial mirror) is directed toward the opposite or second surface of the double-sided mirror (its lower surface). The second or lower surface of the double-sided mirror deflects the beam downwardly again toward the target surface along the longitudinal axis of the instrument. If the instrument is positioned at the proper standoff distance from the surface under evaluation, and the optical axis of the instrument is parallel to the normal vector of the surface under evaluation, the beam deflected downwardly from the double-sided mirror will pass through the apertured photosensor. Part of the optical power of the beam will be intercepted by the photosensor surface facing the double-sided mirror. The remaining portion will be reflected from the surface under evaluation. Part of the beam reflected from the surface under evaluation is intercepted by the apertured photosensor facing the surface under evaluation. Another portion of the beam reflected from the surface under evaluation will be deflected by the mirrors back into the light source, repeating the optical path in reverse direction. If the optical axis of the instrument is parallel to the normal of the surface under evaluation, but the distance between the instrument and the surface is different from the determined standoff distance, the light spot as intercepted by the upper side of the photosensor will be displaced on a horizontal axis, i.e. laterally across the surface of the photosensor parallel to a line between the second and third mirrors. Likewise, if the standoff distance differs from the distance to the surface under evaluation, and if the normal vector is not parallel to the longitudinal or optical axis of the instrument, the light spot on the photosensor will be displaced in the plane of the upper photosensor in a direction dictated by the amount of the deviation mentioned.

When the instrument is to utilize interferometer principles, the beam emanating from the light source passes through an upper or first apertured photosensor and is split into two parts by an axial beam splitter which replaces the double-sided mirror. One part is directed toward the target surface through an apertured photosensor. The other part is directed to the first non-axial mirror which, as mentioned, is tilted so that the beam makes an angle $\beta$ with a line normal to the target surface. From the non-axial mirror, the beam is reflected to the surface under evaluation. The surface under evaluation deflects the beam toward the second mirror from which it is deflected to the beam splitter. The beam splitter again divides the beam. One portion of the beam travels to the first mirror and, passing through the beam splitter, continues to circulate in a counterclockwise direction while subjected to periodic splits by the beam splitter. The other portion of the beam travels to the surface under evaluation through a second apertured photosensor. Two interfering beams exist in this case: one travels straight through the beam splitter from the source, while a second is subjected to periodic splits while traveling in a counterclockwise direction. A second apertured photosensor which faces the beam splitter intercepts the two interfering beams. These two beams interfere with each other as a function of difference in their respective optical paths. As the two beams are reflected from the surface under test, part of them is intercepted by the photosensor facing the surface. The reflected beams are split by a beam splitter. One part of each of the reflected beams is traveling toward the light source via an apertured photosensor above the beam splitter, and the other parts are directed toward the second mirror and will be circulating in a clockwise direction and subjected to periodic splits by the beam splitter that directs a portion of these beams to the light source via the second apertured photosensors, creating an interference pattern. The difference between the interference patterns of the two photosensors facing the beam splitter is proportional to displacement of the surface under evaluation from the standoff distance, and from deviation between a normal to the surface and the optical axis of the instrument.

In both cases (although by different methods), the signal conditioning hardware can produce the following information: vertical and angular deviations from the standoff distance as represented by a vector between the instrument and the normal vector of the surface under evaluation, and the reflectance characteristics of the surface under evaluation as a function of distance.

THE FIGURES

Refer now to the figures, which illustrate the invention by way of example.

FIG. 1 is a diagram of a distance measurement photometer in accordance with the invention when employing a reflective/refractive method;

FIG. 2 is a plan view of an apertured radially segmented photosensor assembly;

FIG. 2A is the bottom view of FIG. 2;

DETAILED DESCRIPTION OF THE INVENTION

Figure 1A:
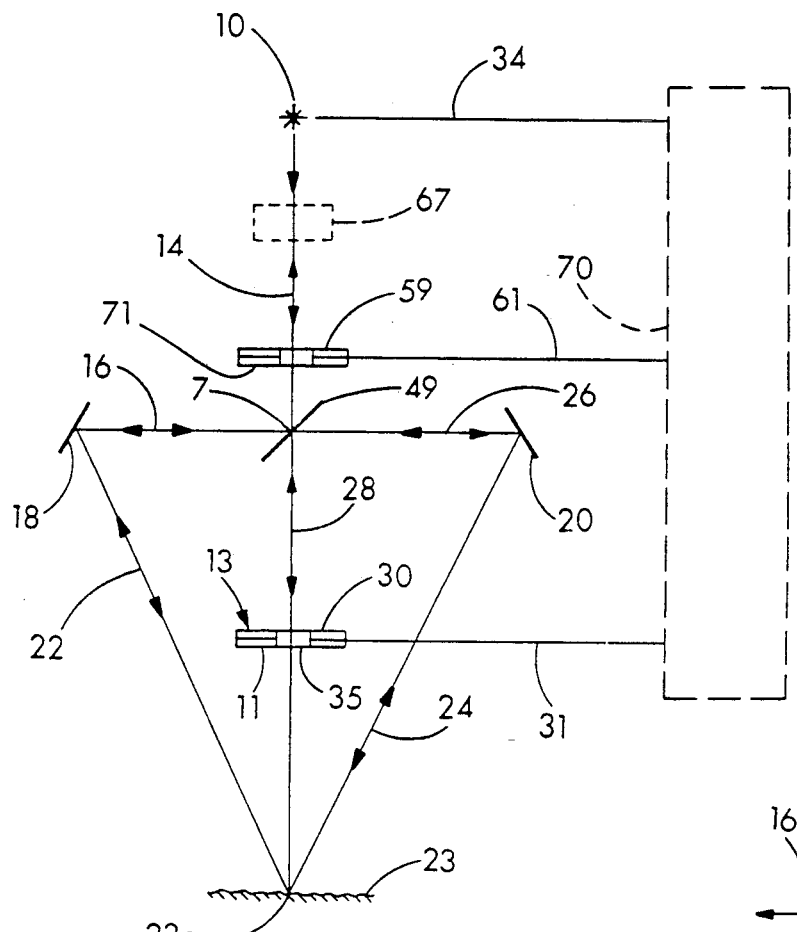
FIG. 1a is another view similar to FIG. 1 but illustrating the invention when employing photometer-interferometric principles.

The description will start with a description of the invention employed as a reflective/refractive distance measurement photometer instrument.

Refer now to FIG. 1. Light source 10, which can be a laser diode, a laser, a Light Emitting Diode or another collimated light source with known physical properties, projects a longitudinal axial beam identified by numeral 14. Note that all beams are illustrated by single lines for the sake of clarity. In reality they have a certain width or profile. The longitudinal axial beam 14 encounters a double-sided mirror assembly 12, also identified by a single line. The upper mirror surface 19 of double-sided mirror 12 and the axis of beam 14 intersect. This intersection creates a point in space 7, which is a point of dimensional reference of Xo, Yo, Zo coordinates. Beam 14 is deflected from mirror surface 19 along a horizontal lateral line represented by numeral 16 to a non-axial or lateral mirror 18 which is fixed at an inclined angle $\beta$ to the optic axis 14. Mirror 18 deflects the beam along line 22 forming an angle $\beta$, to target surface 23. Target surface 23 deflects the beam along line 24 to mirror 20. A lateral mirror 20 which is positioned at a fixed angle $\beta$ with respect to the optic axis 14 deflects the beam along line 26 toward mirror surface 9 of the double-sided mirror assembly 12, forming an angle $\beta$ between and beam 26. From mirror surface 9, the beam is deflected along the line represented by numeral 28 through aperture 33 of photosensor assembly 30 to target surface 23. The line identified by numeral 28 is the optical axis of the instrument.

The assembly 13 comprises two back-to-back photosensors 30 and 11 having an aperture 33, the upper one 30 comprising, for example, four segments 30a-30d and the lower one 11 comprising, for example, four segments 11a-11d. Each segment is connected to signal conditioning hardware 21 by conductors 31a-31e and 11a-11e shown in FIGS. 2 and 2A. Each such photosensor can be obtained, for example, from Silicon Detector Corp., Camarillo, Calif. (part no. SD150-41). While the signal conditioning circuitry 21 can be any suitable circuit known to those skilled in the art or available commercially, preferred signal conditioning devices comprise a circuit for comparing received signals. The signal conditioning hardware 21 preferably includes circuitry for two kinds of comparisons: one, a comparison among the signals from the segments of the single photosensor and another for comparing the total signal from the upper photosensor of a back-to-back pair with the total signal from its lower back-to-back counterpart.

Beams at 14 and 28 are located on the optical axis of the instrument. Part of the power contained in the beam traveling downward along line 28 is intercepted by photosensor 30. If the normal of the target surface 23 coincides with the optical axis defined by line 28, and if the surface 23 is at a calibrated standoff distance from the instrument represented by the surface at the position 23 in FIG. 1, then the reflected light from the surface 23 travels along axis 28 through aperture 32, back again along lines 26, 24, 22 and 16 in a clockwise direction, and at 14 toward the light source 10. While passing up through aperture 33, the part of the optical power contained within the reflected beam is intercepted by photosensor 11 that faces surface 23 under examination. The standoff distance of the instrument is defined as the distance between two points: the first point identified by numeral 23a created by the intersection of lines 28 and 22 and the second point identified by numeral 27 created by the intersection of line 26 with the lower reflective surface of mirror 9.

FIG. 1 shows an optional lens identified by numeral 41. The photosensor assembly 13 connections to signal conditioning hardware 21 are represented by a single line 31. The light source 10 connections to the signal conditioning hardware 21 are also identified by a single line numeral 34.

The operation of the instrument will now be described. If the normal of surface 23 coincides with the optical axis 28 and if the distance between point 23a of surface 23 and point 27 is equal to the standoff distance as previously defined, then upper photosensor 30 will intercept a portion of the optical power contained within the beam traveling downwardly along axis 28. The portion of the beam intercepted by photosensor 30 forms a ring-shaped light spot identified by numeral 28 in FIG. 2. If, however, the surface 23 is displaced downwardly toward a line represented by numeral 25 while the normal of the of the surface is parallel to the optical axis 28, the normal of the surface 23 and the beam traveling downwardly along line 22 will intersect the surface at its new location at point 25a. The beam will then be reflected along lines 36, 38 and 40. As a result of change in surface position from 23 to 25, the ring-shaped light spot will move horizontally leftward on the face of photosensor 30 to a position indicated by dotted lines and numeral 40 in FIG. 2. Likewise, if the surface 23 under evaluation is displaced upwardly above point 23a in FIG. 1, the light spot will move horizontally to the right (not shown) on photosensor 30. If the normal of the surface represented by line 25 does not coincide with the optical axis 28 while maintaining the standoff distance between surface and instrument, the light spot will change its shape and position on the photosensor 30, depending upon the angle to which the instrument is tipped. Likewise, if the distance between the instrument and surface under evaluation is not equal to the standoff distance, and if the optical axis 28 of the instrument does not coincide with the normal of the surface, the light spot will move on the face of photosensor 30 as a function of surface relative displacement from the standoff distance and the angular displacement of the normal of the surface 23 from the optical axis 28 of the instrument. Therefore, because of the variation in the relative strength of the signals through lines 31a-31e to the signal conditioning hardware 21, the instrument provides the capability of maintaining a predetermined standoff distance between the instrument and surface 23 under evaluation in such a way that the optical axis 28 of the instrument coincides with the normal of the surface 23 under evaluation. To accomplish this, only one segmented apertured photosensor 30 is used. If desired, the function of proper standoff position determination can be performed by a segmented photosensor without an aperture 33. Once the distance between the instrument and the surface 23 under evaluation is equal to the standoff distance, the beam reflected from surface 23 along axis 28 represents the reflectance of surface 23 around a point 23a. The segmented apertured photosensor 13 intercepts a portion of this reflectance.

When the instrument's optical axis coincides with the normal of the surface at the predetermined standoff distance, the measured characteristic of the specimen 23 is the reflectance of the specimen. This is measured as a function of the signals obtained from the upper photosensor 30 receiving light from source 10 and the signals from the lower photosensor 11 which receives light reflected directly from the specimen onto the lower photosensor. The signal conditioning hardware 21 that is connected to the photosensor assembly 13 provides information about both the displacement of surface 23 from the standoff distance of the instrument and the displacement of the normal of surface 23 from the optical axis 28 of the instrument, and the reflectance characteristic of surface 23 around point 23a.

Figure 3:
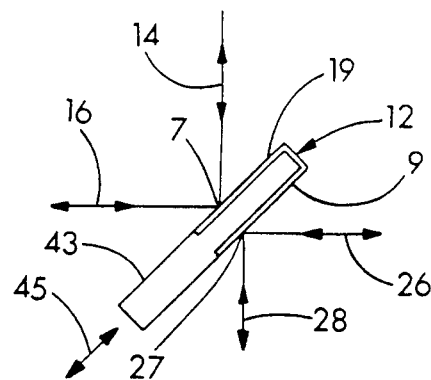
FIG. 3 is a detailed side elevational view of a double-sided mirror assembly.
Figure 3A:
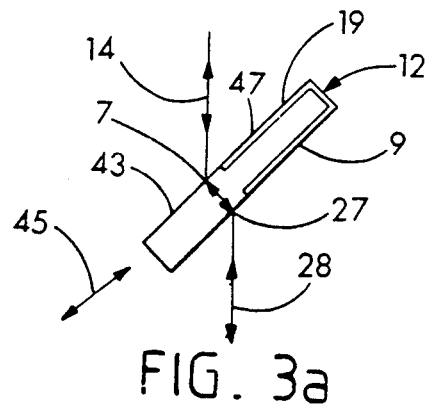
FIG. 3a is a detailed side elevational view of a double-sided mirror assembly.

FIGS. 3 and 3a illustrate one example of a double-sided mirror assembly 12 and its effect on the beam path. FIG. 3 shows an expanded view of the double-sided mirror and its interaction with the beam traveling along lines 14, 16, 26 and 28. The mirror layers 9 and 19 are deposited on glass plate 43. When desired, the double-sided mirror assembly 12 is displaced along the line represented by numeral 45. The thickness of the glass plate 43 and its index of refraction should be such that their combined effect on the beam traveling along line 14 will provide an optical path connection represented by a refracted beam line 47 between dimensional reference point 7 and point 27 to carry the beam downwardly along the optical axis at 28.

To avoid interception of diffused reflectance resulting from angular illumination of surface 23 by the beam that travels along lines 22 and 24 once the surface is properly positioned in relationship to the instrument, one displaces the double-sided mirror assembly 12 from the position of FIG. 3 to the position of FIG. 3a. The displacement of double-sided mirror assembly 12 can be accomplished manually, electromechanically or by several other means. Once the mirror assembly 12 is displaced, the beam from light source 10 will pass straight down along line 14 and through diffraction with the glass layer along line 47 will continue to travel along the optical axis 28 without encountering lateral, i.e. non-axial, mirrors 18 and 20.

Mirrors 18 and 20 are shown as plane stationary mirrors only for the sake of example. The mirrors can have different shapes and can be mechanized in many different ways, e.g. by tilting them simultaneously to different angles other than the angle $\beta$ to create a variable standoff distance.

FIG. 2 shows the arrangement of photosensitive segments (four) used (30a–30d) as a part of the double-sided photosensor assembly 13. Conductors 31a–31d carry the signals produced by respective segments to the signal conditioning hardware 21. These signals are proportional to the optical power received by the respective segments 30a–30d. Conductor 31e represents a signal return conductor for photosensor 30, which is common to all segments. Likewise, as shown in FIG. 2A, beneath photosensor 30 is the radially segmented apertured photosensor 11 that is mounted in a back-to-back relationship to photosensor 30. The photosensor 11 has four segments 11a–11d and five contacts 31f–31j which operate in the same way as in the photosensor 30.

Refer now to FIG. 1a for the description of the instrument of the present invention when made to employ interferometric principles and wherein the same numerals correspond to parts already described. For the time being, assume that the distance between surface 23 under evaluation and the instrument is equal to the standoff distance of the instrument and that the normal of the surface 23 coincides with the optical axis 28 of the instrument. The instrument has the same mirrors 18 and 20 and the same photosensor assembly 13. Numeral 49 designates a beam splitter (which replaces the double-sided mirror assembly in FIG. 1) positioned at a 45° angle to the optical axis coinciding with light of the beam from the source 10 on line 14. For the sake of simplicity, the beam splitter 49 is identified by a single line. The beam from the coherent light source 10 travels along line 14 through an optional but preferred optical isolator 67 and through an upper segmented double-sided photosensor assembly 59 to beam splitter 49. The photosensor assembly 59 is connected to signal conditioning hardware 70 by conductors designated generally by numeral 61.

Signal conditioning hardware 70 has suitable circuitry for comparing the currents from the segments of the photosensor 59 and includes common elements and components of the same kind used in signal conditioning hardware 21 of FIG. 1. The signal conditioning hardware 70 provides circuitry for comparison of interference signals resulting from the difference between optical paths, as will be described.

In case the light source 10 is a laser diode or other laser and its coherence may deteriorate as a function of the reflected light into it, an optical isolator 67 (such as a Faraday type isolator) will prevent such coherence damaging reflections from entering the light source 10. At a dimensional reference point 7 that is established by the intersection of beam splitter 49 with the optical axis 28 of the instrument on line 14, the beam is divided into two parts. One part travels leftward along line 16 and the other travels downward along the axis 28. The beam that travels leftward follows a general counterclockwise direction as described by lines 16, 22, 24 and 26. While it cycles along lines 16, 22, 24 and 26 during each such cycle, it is subjected to periodic splits by beam splitter 49 that directs a portion of counterclockwise cycling beam downward along the path of line 28, the optical axis of the instrument. Thus, there are created two beams of different optical path lengths that travel downwardly along axis 28: the counterclockwise circulating one and the other beam directly from the source 10. A portion of the power contained within each of these two interfering beams is intercepted by photosensor 30. The combined signal sensed by the upper photosensor 30 is an optical interference pattern created by the difference in the optical path lengths between a beam that travels straight downward from light source 10 and the beam traveling in a counterclockwise direction while subjected to periodic splits downward. The portion of both of these beams that continues to travel along line 28 to surface 23 is reflected upwardly along axis 28. A portion of the two interfering beams that are reflected upwardly from surface 23 is intercepted by photosensor 11, and the remaining portion travels upwardly to the beam splitter 49 where the two interfering beams are split. One part of the two beams travels upward along line 14 and the reflected part travels along lines 26, 24, 22 and 16 in a clockwise direction, in which the beams are continuously cycling while subjected to periodic splits by beam splitter 49. During each such split a portion of the beam travels along line 14 upwardly through the photosensor assembly 59, which can be identical to photosensor assembly 13. The lower surface 71 of photosensor assembly 59 intercepts a portion of the optical power of the beams traveling upwardly along line 14. There are two types of beams that travel upwardly and are intercepted by the photosensor assembly 59: the interfering beams that travel upwardly from point 23a straight through beam splitter 49, and second, the portion of the interfering beams that cycle in a clockwise direction. These two sets of beams have different optical path lengths. The additional interference due to the difference in optical light path lengths between these two sets of beams will be sensed by the lower surface 71 of photosensor assembly 59. In this embodiment, one of the photosensors is a lower photosensor assembly 13 positioned between the beam splitter 49 and the specimen. The lower photosensor assembly 13 comprises a photosensor assembly having a pair of upper 30 and lower 11 back-to-back segmented photosensors with aligned apertures. The lower photosensor 13 receives interference beams that are reflected upwardly from the target surface 23.

Any deviation of surface 23 and its normal from the standoff distance and the optical axis will alter the interference characteristics as sensed by photosensor assemblies 13 and 59. For standoff distance position acquisition, one can use single-sided apertured segmented photosensor 30 and 71, although double-sided assemblies such as 13 and 59 improve overall accuracy and can indicate changes in beam polarization, for example. The difference between the optical power received by the upper photosensor 59 and lower photosensor 13 is compared to indicate the reflectance of the specimen as a function of the optical power reflected directly from the specimen along the optical axis onto the lower photosensor of the pair.

Refer now to optional components 73–79 which can be used in another embodiment of an instrument based on the reflective/refractive method illustrated in FIG. 1 to obtain reflectance measurements at other than standoff distances. As shown below, the double-sided mirror assembly 12 on axis 28 is a beam splitter 79. An additional collimated light source 73 projects a beam along line 77. The beam is split into two parts. The part of interest is directed by beam splitter 79 along the optical axis 28 downwardly to surface 23. Assuming the instrument is properly aligned with the surface, i.e. that the normal of surface 23 coincides with the optical axis 28, the beam will be reflected from surface 23 along optical axis 28. Part of the reflected beam is intercepted by photosensor 11; the rest of the beam passes through the aperture 33 of photosensor assembly 13 to beam splitter 79. Light source assembly 73 is connected by conductors 75 to signal conditioning hardware 21. Signal conditioning hardware 21 also controls the turn on/off sequence of light sources 10 and 73. For example, when light source 73 is on, light source 10 is off and vice versa.

Signal conditioning hardware 21 also provides reflectance information as sensed by photosensor 11 and position information of surface 23 as sensed by the photosensor 13.

Several factors concerning the improved sensitivity of the invention will now be discussed. In addition to the above mentioned features of the instrument, it should be noted that, in general, the sensitivity of most, if not all, instruments operating based on detection of directional change of reflected light due to angular deviation of a surface depend on the distance between the point of reflection from the surface and the location of the photosensor. Thus, the reflective members 27, 18 and 20 of FIG. 1 provide increased sensitivity to angular deviation because they increase the optical path length. Consequently, the angular deviation will be detected more accurately by the segmented apertured photosensor 30. If space constraints are equal, the instrument described in FIG. 1 provides greater sensitivity to angular deviation than other such instruments. Furthermore, if the normal of surface 23 has only a slight deviation from the optical axis 28, while surface 23 is at the calibrated standoff distance, light projected from the light source 10, and reflected as explained above onto photosensor 30 will cause the central aperture 33 to pass a particular amount of light to the surface. This light beam will then be reflected from surface 23 in an upward direction not parallel to the optical axis 28, but dependent on angular deviation of surface 23 from optical axis 28. The reflected light will be intercepted by photosensor 11 which can determine its optical power, thus providing additional information and sensitivity to the measurement of such angular deviation of the surface 23.

In addition to these improvements in sensitivity, it should also be understood that photosensor 11 has an additional role in improving the accuracy of sensing the displacement of the surface 23 from the standoff distance. If only photosensor 30 and light source 10 were used to determine displacement of surface 23, there will be an overall error associated with three parameters that describe such a displacement. However, separation of the overall error into three parameters (distance and two angles) associated with the displacement is a major problem not addressed by other instruments. Since the role of photosensor 11 and light source 10 in the context of sensing displacement of surface 23 from calibrated standoff conditions is to sense only angular displacement of the surface, the error associated with longitudinal displacement can be better quantified and reduced. In addition, further improvements in instrument performance are made with the use of the photosensor 11 in conjunction with the light source 73. It provides additional information about angular displacement of the surface.

In addition, the accuracy of the instrument of FIGS. 1, 3 and 3a can be improved if the shiftable double-sided mirror 12 will be deposited on a beamsplitter 49 of the kind shown in FIG. 1a. In such case, the reflective/refractive instrument may be used for coarse surface displacement measurement while the interferometric instrument can be used for fine surface displacement measurement.

Figure 4:
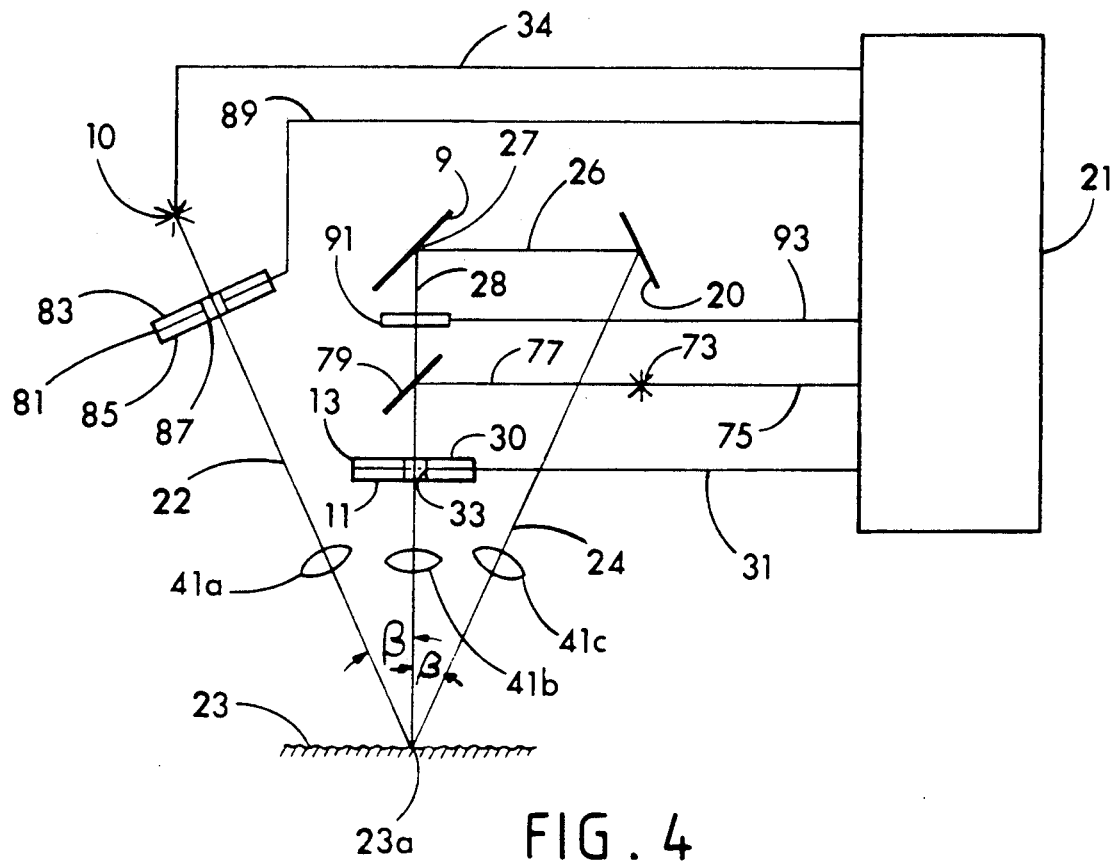
FIG. 4 is another embodiment of the invention.

Refer now to FIG. 4 which illustrates another preferred implementation of the instrument. In this embodiment, the light source 10 which is positioned to one side of the optical axis 28 provides a beam 22 at an angle $\beta$ with respect thereto. Mirror 18 is omitted, a photosensor 81 is provided, and a shutter 91 is provided between reflective member 12 and photocell 30. Three lenses 41a–41c can be placed in the path of beams 22, 24 and 28 proximate to the surface 23. Corresponding numbers refer to the same parts already described in FIGS. 1, 2, 2A, 3 and 3A.

The principle of operation of the embodiment of FIG. 4 is generally the same as was described for FIG. 1, however, there are some advantages to such an implementation. Again, for the sake of explanation, initially assume that the instrument is at a calibrated standoff distance from surface 23 and that the normal of surface 23 coincides with the optical axis of the instrument. A collimated light source 10 projects a beam along line 22 to illuminate the surface 23 at an oblique angle. The beam along line 22 intersects surface 23 at point 23a. It is reflected from point 23a along line 24 forming an angle of reflection $\beta$ with surface 23 that is equal to the angle $\beta$ of oblique illumination. The beam reflected from point 23a is intercepted by a non-axial reflective member 20. The non-axial reflective member reflects the beam along line 26 toward an axial reflective member 9. The point of intersection between the axial reflective member 9 and line 26 establishes a reference point 27. All major components of the instrument are positioned at known distances from point 27. Axial reflective member 9 reflects the beam downwardly along the optical axis 28. Optical axis 28 intersects beam path 22 and surface 23 at point 23a, thus defining the angle of incidence $\beta$. As the light travels downwardly along the optical axis 28, a portion of it is intercepted by apertured segmented photosensor assembly 30. The other portion travels through opening 33 along optical axis 28 toward surface 23. Thus, the intersection of the line 22 and the optical axis defines the point 23a. As the beam reflects off surface 23 upwardly along optical axis 28, it is directed by reflective members 9 and 20 back toward point 23a on surface 23. From surface 23, it is directed along line 22 back to light source 20. On optical axis 28, between axial reflected member 9 and double-sided apertured photosensor 13 is located an additional reflective member, beam splitter 79. Beam splitter 79 directs light projected from a light source 73, preferably collimated, downwardly along optical axis 28. All explanations of the mechanics of light spot displacement over the surfaces of photosensors 30 and 11, as a function of surface 23 for FIG. 1, are directly applicable to FIG. 4.

So far, it has been explained that the deviation (angular or longitudinal) of surface 23 from the calibrated standoff conditions is sensed primarily by photosensor 30. The accuracy of determining such deviation can be increased by use of data derived from photosensor 11 that faces surface 23. For small angular deviations of the normal of surface 23 from the optical axis 28, a substantial amount of light originating from light source 10 will pass through aperture 33 in a generally downward direction dependent on the angular deviation of surface 23. This light beam intersects with surface 23 at a point spaced away from point 23a on a part of surface 23. As surface 23 reflects the beam upwardly, it is intercepted by photosensor 11. The optical power distribution among the segments 11a–11d of photosensor 11 provides additional information about the angular deviation of normal of surface 23 from optical axis 28.

To further improve position detection sensitivity, one may use lenses 33a, 33b and 33c axially located on lines 22, 24 and 28. These lenses will reduce the light spot size as projected or reflected around point 23a. Such lenses may be stationary or movable, depending on the need of application.

In addition to the already explained method of reflectance measurements for FIG. 1, and as it applies to FIG. 4, it should be clarified that illumination of the surface 23 by light source 73 is one reflectance measurement as derived from the signals of photosensors 11 and 30. However, reflectance can be separated into several categories, such as a) normal reflectance as a function of vertical deviation from standoff position and b) near normal as a function of angular and vertical deviation of the surface 23 from the calibrated standoff position. The second reflectance is measured based on the beam of non-axial light source 10 and is the normal reflectance measurement at a fixed standoff distance. However, this second reflectance measurement is not necessarily equal to the first reflectance measurement, and it strongly depends on the roughness of surface 23. The third reflectance measurement is c) one which corresponds to illumination by beam 22 from light source 10 onto surface 23 at an oblique angle. To measure angular reflectance c), an additional apertured segmented photosensor can be used. It may be a single-sided photosensor or a double-sided photosensor facing the surface 23. Such a photosensor is located axially on line 22 and marked by numeral 81. Photosensor 85, double-sided or single-sided, is the same type as photosensor 13 and is connected to signal conditioning hardware 21 by conductors designated by numeral 89. The side facing light source 10 is identified by numeral 83. The opposite side is identified by numeral 85. The optical power of light source 10 that is partially intercepted by photosensor 83 travels through aperture 87 along line 22 to surface 23 and, after reflections from surface 23 and subsequent reflections off members 20 and 9, is partially intercepted by photosensor 30. With this arrangement, one can establish angular reflectance due to illumination of the surface at an oblique angle by measuring the relationship between the optical power projected as sensed by photosensor 83 and the optical power reflected as sensed by photosensor 30.

To further improve reflectance measurements, one may add beam blocking means, e.g., beam shutters between reflective members 9 and 79 generally identified by numeral 91. The purpose of the shutters is to prevent multi-directional simultaneous reflections from surface 23. In the alternative to the configuration shown, one may insert the shutter 91 below photosensor 30, if desired. When measuring reflectance as a function of illumination by light source 73 and signals from photosensors 30 and 11, the beam traveling along line 28 is blocked by a shutter identified by a single line numeral 91 located between reflective members 9 and 79. In general, the shutter operation can be activated at a selected time as controlled by signal conditioning hardware 21. If so, the activation and control lines for shutter 91 are identified by a single numeral 93. There are many different means available to implement such beam blocking or interruption. Under such circumstances, light source 10 will be turned off.

The invention can also be used as a radiometer for measuring radiation from surface 23. A special preferred configuration of the instrument is related to radiation measurements of surface 23. In many instances, there is a need to accurately position a radiometer in relation to a radiating surface 23 and to measure surface 23 radiation. To use the instrument of FIG. 4 for radiation measurements, one may use two different types of photosensors as parts for photosensor assembly 13. In such a case, photosensor 30 of photosensor assembly 13 is the same as previously described. However, photosensor 11 is made transparent to the light sources 10 and 73 and is unaffected by beams from these sources. Photosensor 11 is made sensitive to radiation originating at surface 23. Thus, the function of measurement of displacement of surface 23 from calibrated standoff conditions is based on the signals sensed by photosensor 11 other than from sources 10 and 73 and optionally by photosensors 83 and 85. Reflectance sensing is accomplished by using photosensors 11 and 83, and optionally photosensor 85, while the radiation is sensed by photosensor 11 having a center 11a that does not have an aperture 33 but is transparent to light sources 10 and 73. Such photosensor 11 may be segmented, and each segment may have a specific spectral characteristics as needed to measure radiation from surface 23.

Figure 5:
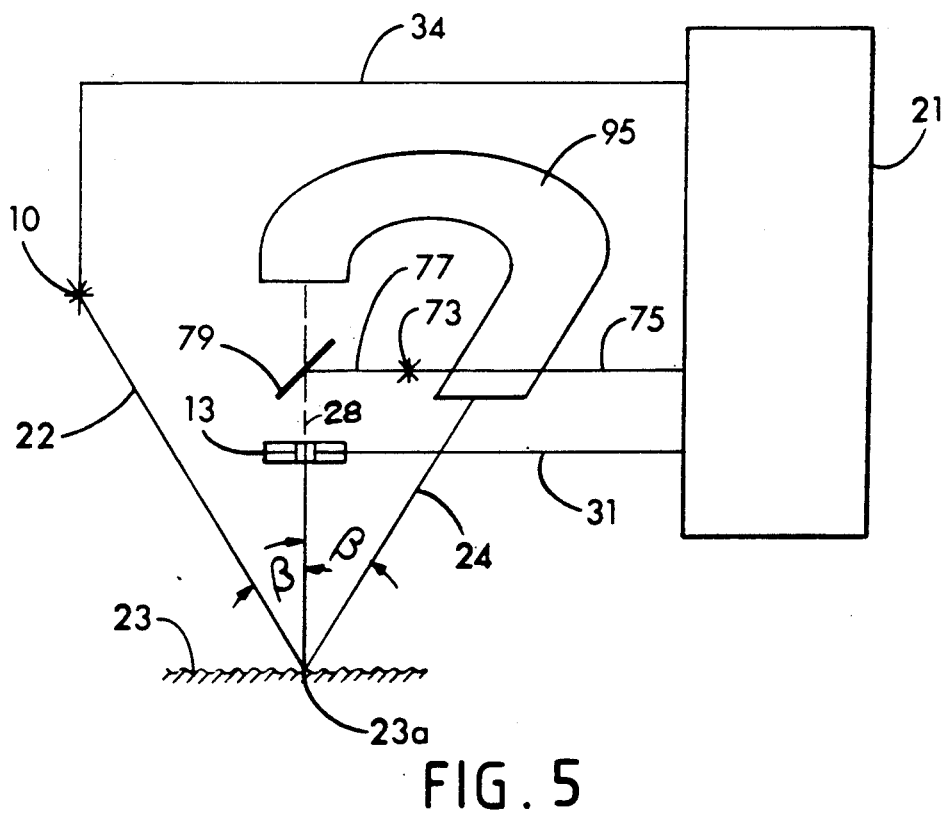
FIG. 5 is still another embodiment of the invention.

FIG. 5 shows yet another preferred implementation of a similar concept. For the sake of clarity, many components as described for FIGS. 1 and 4 can be employed but are omitted for clarity of illustration. In this embodiment, a fiber optic bundle or other waveguide 95 is placed with one cut and polished end positioned to receive the light beam 24 reflected from surface 23. The other end is positioned at the opposite end of the optical axis 28 from surface 23. The function of reflective members 9 and 20 as shown in FIG. 4 is replaced by the multistrand or other waveguide 95. While the configuration illustrated in FIG. 5 makes possible similar beam paths to those shown in FIGS. 1 and 4, it has certain performance/cost advantages as compared to the configurations described in FIGS. 1 and 4.

One of the unique features of the instruments described in FIGS. 1, 1a, 4 and 5 is the ability to control the intersection of multiple beams by precisely positioning the mirrors (and optionally the lenses 41a–41c). By controlling the intersection of several beams, one controls the common volume of the beams engaged in the intersection, and the amount of optical power contained within such a volume. In general, the larger the number of such intersections that can be accomplished by the use of additional beam deflective members, the more accurately one may derive surface displacement from a calibrated standoff distance and reflectance characteristics of the surface under evaluation.

As for the instrument illustrated in FIG. 1a, if not used for surface reflectance measurements, i.e., in applications in which surface 23 is not displaced and is highly reflective, e.g. mirror-like, the signals produced by photosensor assemblies 13 and 59 will be descriptive of displacement of the instrument itself.

While FIGS. 1, 1a, 4 and 5 show a double-sided photosensor 13 located on axis 28, the preferred location of photosensor 13 may be dictated by a specific application and the type of lenses selected for such an application. For example, in FIG. 4 photosensor 13 may be placed axially along line 26. Such a change of placement of photosensor 13 will require proper placement of shutter 91, beam splitter 79 and light source 73.

Many variations of the present invention within the scope of the appended claims will be apparent to those skilled in the art once the principles described above are understood.

What is claimed is:

1. An optical instrument for measuring the characteristics of a specimen having a surface comprising, a light source to provide a beam of light directed at an oblique angle $\beta$ with respect to the normal of the surface, said beam being reflected from the surface at the same angle $\beta$ with respect to the normal of the surface, said instrument having an optical axis normal to the specimen, a first photosensor means optically aligned with the reflected beam for receiving the reflected beam when the specimen is at a selected standoff distance from the instrument, said photosensor including means to detect movement of the reflected beam thereon responsive to changes in the distance of the instrument from the standoff distance and to changes in the orientation of the surface with respect to the instrument which alters the point at which the reflected beam strikes the photosensor, said photosensor thereby providing signals responsive to changes in the orientation and distance between the specimen and the instrument, means providing a second beam of light directed away from the specimen along said optical axis, and a second photosensor means optically positioned to receive the second beam of light for measuring a characteristic of the specimen.

2. The optical instrument of claim 1 wherein beam redirecting means is provided for redirecting the reflected beam onto the specimen along said optical axis, means is provided for directing an additional beam of light along the optical axis onto the surface of the specimen, and a beam blocking means is provided for intercepting the redirected beam to then prevent oblique illumination of the surface of the specimen for isolating the measurement of at least one of said photosensor means to illumination reflected from the specimen at a single angle.

3. The optical instrument of claim 2 wherein a first axial reflective means is provided for deflecting the reflected beam onto the specimen along said optical axis, a second reflective means is positioned on the optical axis for deflecting a beam from a second source of light along the optical axis onto the surface of the specimen and said beam blocking means is a shutter located between the two axially positioned reflective means.

4. The optical instrument of claim 2 wherein said photosensor means are connected to signal conditioning circuitry means, said signal conditioning circuitry includes means for activating and deactivating the beam blocking means to thereby prevent oblique illumination of the surface of the specimen at a selected time.

5. The optical instrument of claim 1 including lenses positioned to reduce the size of light spots projected by said beams onto the surface of the specimen to thereby improve measurement of longitudinal and angular deviation of the surface with respect to the optical axis of the instrument.

6. The optical instrument of claim 1 having a selectively operable means for measuring angular displacement of the specimen with respect to the optical axis of the instrument and for measuring longitudinal displacement of the surface of the specimen along the optical axis whereby angular and longitudinal displacement of the specimen from said standoff position can be measured separately, thereby improving the accuracy of said displacement measurements.

7. The optical instrument of claim 1 including a double-sided, back-to-back photosensor optically aligned with said beam of light positioned normal to the surface of the specimen on the optical axis of the instrument, said double-sided photosensor having an apertured and segmented photosensor on a side thereof facing away from the specimen and a second non-apertured photosensor on a side thereof facing the specimen, said non-apertured photosensor being transparent to light projected from the light source and being adapted to sense radiation emanating from the specimen.

8. The optical instrument of claim 7 wherein signal conditioning circuitry is connected to the double-sided, back-to-back photosensor for independent measurement of a) the angular displacement of the surface and b) the longitudinal displacement of the surface from a known standoff position, and one of said photosensor means is directed toward said surface for measuring radiation impinging thereupon from the specimen.

9. The optical instrument of claim 1 wherein said beam redirecting means includes a double-sided mirror for redirecting the reflected beam onto the specimen along the optical axis and said instrument operates to measure characteristics of the specimen through a reflective/refractive regimen.

10. The optical instrument of claim 1 wherein said beam redirecting means includes a beam splitter positioned on the optical axis to direct said beam toward the specimen along said optical axis and said instrument measures characteristics of a specimen through an interferometric regimen.

11. The optical instrument of claim 9 including means therein for sensing self-displacement with respect to the specimen.

12. The optical instrument of claim 1 wherein said beam redirecting means comprises a waveguide.

13. The optical instrument of claim 12 wherein said waveguide comprises a fiber optic bundle.

14. The optical instrument of claim 1 having beam reflecting means that directs the beams projected onto said surface and reflected from said surface to be reflected so as to intersect each other at the specimen and by decreasing the common volume of the beams engaged in said intersection maximizing the optical power contained within such volume to thereby improve the accuracy of measurements made by said instrument.

15. The optical instrument of claim 1 wherein said source of light for providing a beam of light intersecting the specimen at an oblique angle comprises a source of light positioned to one side of the optical axis of the instrument and a back-to-back apertured photosensor means is positioned between the light source and the specimen for measuring a characteristic of the specimen.

16. The optical instrument of claim 1 wherein said source of light for providing a beam of light intersecting the specimen at an oblique angle comprises a source of light positioned to one side of the optical axis of the instrument and a waveguide means is provided in the instrument for redirecting the beam reflected from the specimen to travel along the optical axis of the instrument toward the specimen.

17. The optical instrument of claim 1 wherein said source of light for providing a beam of light intersecting the specimen at an oblique angle comprises a source of light positioned to one side of the optical axis, wherein a second source of illumination is provided for illuminating the specimen and reflective means is provided on the optical axis of the instrument for directing light from the second source of illumination onto the specimen along the optical axis thereof, said light sources being operable independently of one another to make possible the separate measurement of beams reflected from normal and oblique illumination to thereby enhance the accuracy of the instrument.

* * * * *